United States Patent [19]

Katakura et al.

[11] Patent Number: 5,075,107
[45] Date of Patent: Dec. 24, 1991

[54] DENTURE PLATE ADHESIVE SOFT LINER OR GELLING TISSUE CONDITIONER

[75] Inventors: Naoyuki Katakura; Hisao Honma; Makoto Hosotani; Kazunori Iijima, all of Sendai, Japan

[73] Assignee: G-C Dental Industrial Corp., Tokyo, Japan

[21] Appl. No.: 533,775

[22] Filed: Jun. 6, 1990

[30] Foreign Application Priority Data

Jun. 19, 1989 [JP] Japan .................................. 1-154712

[51] Int. Cl.$^5$ ......................... A61K 6/08; A61K 31/78
[52] U.S. Cl. ...................................... 523/120; 106/35
[58] Field of Search ........................... 106/35; 424/81

[56] References Cited

U.S. PATENT DOCUMENTS 4,248,807  2/1981  Gigante ................................. 264/18

FOREIGN PATENT DOCUMENTS 1232808  5/1971  United Kingdom .

OTHER PUBLICATIONS

Jones et al., GA 105:66404c (1986).
Niekawa, GA 106:9342c (1987).
Kalachandra et al., GA 111:102657x (1989).
Katakura et al., GA 111:1601459 (1989).

Primary Examiner—Shep K. Rose
Attorney, Agent, or Firm—Oblon, Spivak, McClelland, Maier & Neustadt

[57] ABSTRACT

A dental composition comprises a powdery component and a liquid component, which are mixed together to use it as a tissue condition, (a) the powdery component is at least one of a copolymer of butyl methacrylate with ethyl methacrylate or a mixture of poly butyl methacrylate with poly ethyl methacrylate, and (b) the liquid component is at least one of butyl phthalyl butyl glycolate (BPBG), dibutyl phthalate (DBP), benzylbutyl phthalate, benzyl benzoate, ethyl benzoate, butyl benzoate and amyl benzoate.

5 Claims, 2 Drawing Sheets

THE CHANGES-WITH-TIME AT 20°C IN THE TORQUE OF THE RESPECTIVE MATERIALS WITH INCREASES IN THEIR VISCOSITY

THE CHANGES-WITH-TIME AT 25°C IN THE TORQUE OF THE RESPECTIVE MATERIALS WITH INCREASES IN THEIR VISCOSITY

THE CHANGES OF DYNAMIC VISCOELASTICITY OF THE FIVE MATERIALS

DENTURE PLATE ADHESIVE SOFT LINER OR GELLING TISSUE CONDITIONER

BACKGROUND OF THE INVENTION

1. Field of the Invention

The present invention relates to a mucosa-regulating material so-called tissue conditioner used in odontotherapy and, more particularly, to a mucosa-regulating material for denture wearers suffering from intra-oral mucosa deformation or mucositis.

2. Background Art

For a powdery component of tissue conditioners now commercially available, polymers based on poly ethyl methacrylate or copolymers of vinyl chloride with vinyl acetate are used, whereas for a liquid component, a mixed liquid of a plasticizer such as butyl phthalyl butyl glycolate (BPBG for short) with ethanol is employed.

For using the tissue conditioner, the powdery component is mixed with the liquid component to obtain a mixture, which is then cast up on the mucosal side of a denture plate. The denture plate is inserted into the oral cavity in which sophisticated contact of the mixture with the mucosal side of the denture plate is regulated over a time, while keeping it flowable thereon. At the time of curing, the tissue conditioner is separated from the mucosal side of the denture plate, and the mucosal side after treatment is substituted by a fresh denture plate material to make the completed denture plate.

The essential conditions required for the tissue conditioner after the mixing of the powdery component with the liquid component are that:

(1) a tissue conditioner should maintain its combined elastic/viscous properties in the oral cavity over an extended period of time, and (2) a tissue conditioner should possess an adhesion strength sufficient for allowing it to remain bonded to the surface of a denture plate over an extended period of time.

In order to cure the mixture meeting both (1) and (2) within a time usually allowed for clinical handling, however, it was generally inevitable to use ethanol as one liquid component. In other words, ethanol served to swell the powdery component and so increase its affinity with respect to the plasticizer of the liquid components, thereby achieving rapid gelling of the mixture after mixing.

Thus, ethanol was essentially required as one liquid component of tissue conditioners, but was a troublesome material for patients, because when used in the form of a liquid component containing ethanol, it gave stimuli to the intra-oral mucosae of patients, dissolved in saliva or emitted an ethanolic odor uncomfortable for patients.

When used with a denture plate formed of a material based on methyl methacrylate (MMA), ethanol of the liquid component solubilizes the surface of a denture plate or swells itself enough to deform or crack the denture plate. Thus, the denture plate is so decreased in strength or so solubilized on separating-off after curing that it is mechanically bonded to a tissue conditioner, often making its separation difficult.

Thus, to use ethanol as one liquid ingredient poses a problem to both patients and clinicians.

As a result of intensive studies made to solve such problems of tissue conditioners as mentioned above, the present inventors have successfully invented a novel dental composition. More specifically, the dental composition according to the present invention comprises a powdery component consisting of either one of a copolymer of butyl methacrylate with ethyl methacrylate and a mixture of poly butyl methacrylate (PBMA for short) with poly ethyl methacrylate (PEMA for short) and a liquid component consisting of at least one of butyl phthalyl butyl glycolate (BPBG) without ethanol, dibutyl phthalate (DBP), benzyl butyl phthalate, benzyl benzoate, ethyl benzoate, butyl benzoate and amyl benzoate, said powdery and liquid components being mixed or kneaded together for use.

According to the present invention, it has now been found that if the copolymer of butyl methacrylate with ethyl methacrylate or the mixture of PBMA with PEMA is used as the powdery component, a dental composition having its physical properties much more improved than those of tissue conditioners heretofore available can then be obtained even without allowing ethanol to be contained as the liquid component in a plasticizer.

BRIEF DESCRIPTION OF THE DRAWINGS

The present invention will now be explained specifically but not exclusively with reference to the accompanying drawings, in which.

DETAILED EXPLANATION OF THE INVENTION

Tissue conditioners are required to act as an elastomer with respect to a force applied within a short time such as an occlusal force and, then, gently receive and push back such force. Where a weak oppresive force of an intra-oral mucosa acts on a material over a long time as encountered when the deformation of the intra-oral mucosal recovers, on the other hand, the material is required to be deformed through its own viscous properties. It is thus of vital importance to investigate the viscoelasticity of that material in order to learn its required properties. From such a point of view, the viscoelasticity of a tissue conditioner using powders of a butyl methacrylate base copolymer having a properly selected molecular weight has been studied. As a result, it has been found that such copolymer powders have their properties improved over those of conventional materials.

It has also been noted that the powdery component according to the present invention, i.e., the copolymer based on butyl methacrylate or the mixture of PBMA with PEMA differs in molecular structure from denture plate resins and so allows tissue conditioners to be relatively easily separated from denture plates with no clinical difficulty. Since the liquid component contains no ethanol, it is unlikely to drop the strength of denture plates. Nor does it make patients unpleasant due to its tastelessness and odorlessness.

For the powdery component of the constitutional components according to the present invention, a copolymer of 100 mol % of butyl methacrylate with 5 to 50 mol % of ethyl methacrylate or a mixture of PBMA with PEMA is used.

The reason why the copolymer of butyl methacrylate with ethyl methacrylate or the mixture of PBMA with PEMA is used in the present invention without recourse to PBMA alone is that there is a difference in flowability between powder/liquid mixtures.

In order to prove this, the following experimentation was carried out.

Synthetic polymers of 150 to 200 mesh were used as powdery materials, whereas butyl phthalyl butyl glycolate (BPBG) free from ethanol was used as liquid material. These materials under test are shown with a commercially available material in Table 1. The powdery and liquid components, stored in a constant temperature room maintained at a measuring temperature, were mixed at powder/liquid ratios specified in Table 1 for 30 seconds. With a cone/plate type of rotary viscometer (RV2 Type made by HAAKE Co., Ltd. with a cone angle of 1°), changes-with-time in the torque of the samples with increases in viscosity were measured at 1 r.p.m. until a torque meter reached a full scale. Measurement was performed after one minute the initiation of mixing.

TABLE 1

| Materials | Experimental Materials | | |
|---|---|---|---|
| | Powder/liquid (by weight) | Liquid Components | Viscosity of Liquids (cp) |
| BMA homopolymer | 1.1/1.0 | BPBG | 54 |
| BMA/EMA copolymer | 1.1/1.0 | BPBG | 54 |
| GC Soft Liner Powder | 1.1/1.0 | BPBG + Ethanol | 12 |

Figure 1:
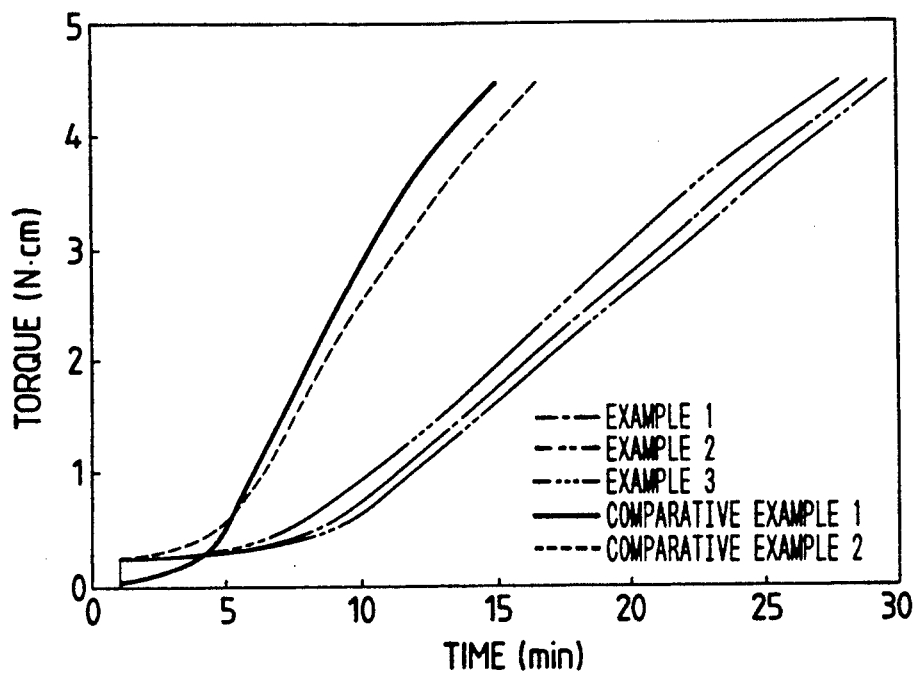
FIG. 1 is a graphical view showing torque changes at 20° C. of examples of the dental composition according to the present invention and comparative examples.
Figure 2:
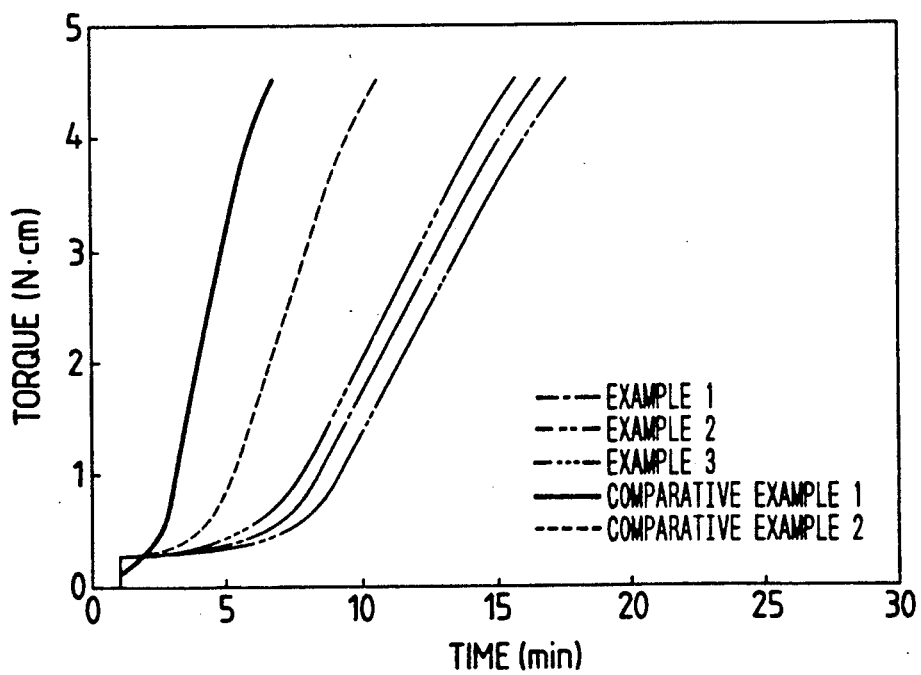
FIG. 2 is a similar graph showing torque changes at 25° C.

BMA: butyl methacrylate
EMA: ethyl methacrylate
BPBG: butyl phthalyl butyl glycolate In what follows, the results of experimentation will be considered. FIGS. 1 and 2 show the changes-with-time in torque at 20° C. and 25° C. of the respective materials with increases in their viscosity. The powder/liquid mixtures all change considerably in flowability under the influence of temperature. From a comparison of FIG. 1 with FIG. 2, it is understood that the samples also differ in flowability depending upon the molecular structure of powders. In other words, the polymer of butyl methacrylate (BMA) alone—Comparative Example 2—is shorter than the copolymer in the time corresponding to the full-scale torque value (about 4.5N·cm) irrespective of temperature.

From a comparison of the data of FIGS. 1 and 2, it is noted that the materials of the present invention (Examples 1-3) are higher than the commercial material (Comparative Example 1) in the torque value at the time of the beginning of measurement and, hence, the viscosity is high immediately after mixing. This is primarily because of the viscosity of the liquid. To put it another way, the viscosity of the liquid of the present material is increased relative to the absence of ethanol, as will be appreciated from Table 1.

It appears that there are no definite standards relating to the so-called gelling-initiation time of dental tissue conditioners. In view of time when powder/liquid mixtures are to be clinically applied over the mucosal surface of a denture plate, parallel investigations were carried out of time when the powder/liquid mixture sold by G-C Dental Industrial Corp. under the trade name of Soft Liner is to be applied at 20° C. According to the results, it is the application time when that mixture shows a torque value of approximately 0.5N·cm. In the present disclosure, the gelling-initiation time is tentatively defined by a time corresponding to this torque value.

From this standpoint, the gelling-initiation time of the respective materials was determined. The results are shown in Table 2.

At 200 mesh or less, the materials in which the copolymer of butyl methacrylate with ethyl methacrylate (Examples 1-2) and the mixture of PBMA with PEMA (Example 3) are used as the powdery component make no noticeable difference in the gelling-initiation time with Soft Liner (Comparative Example 1), whether the temperature is 20° C. or 25° C. However, the material (Comparative Example 2) in which the polymer of butyl methacrylate alone is used as the powdery component is much shorter than Soft Liner (Comparative Example 1) in the gelling-initiation time.

Just after mixing, the powder/liquid mixtures of commercial materials are in the form of a cream of low viscosity, and so are often applied over the mucosal surface of a denture plate, while they are allowed to stand for a length of time of 2-3 minutes, which varies depending upon temperature, thereby increasing their viscosity to a certain extent. Hence, even the polymer alone (Comparative Example 2) may clinically be used, although the time of manipulation has to be slightly reduced at elevated temperature.

Anyhow, it is desired in view of the flowability of powder/liquid mixtures to use the copolymer of butyl methacrylate with ethyl methacrylate or the mixture of PBMA with PEMA in the present invention.

The flowability of tissue conditioners varies under the influence of not only the molecular structure of polymer, temperature, the viscosity of liquid, etc. but also the particle size distribution and molecular weight of polymer, the powder/liquid ratio, the component of liquid, etc.

It is desired that the polymer forming the powdery component according to the present invention have a molecular weight of 100,000 to 1,500,000. At below 100,000, the cured material is so decreased in viscous properties that it becomes hard. At higher than 1,500,000, on the other hand, the cured material is so increased in viscous properties that it becomes too soft, thus failing to act as a tissue conditioner. Preferably, the powdery component according to the present invention has a particle size of 50-600 mesh. At below 50 mesh or in increased particle size, it cannot be used to carry out any proper tissue conditioning and gives stimule to patients. This is because when it is cast up the mucosal surface of a denture plate, its flow therebetween gets worse.

At higher than 600 mesh or in decreased particle size, the powdery component flows satisfactorily between the denture plate and the mucosal surface, but it makes tissue conditioning unfavorable, since it reacts with the liquid component so rapidly that the gelling-initiation time can shorten.

Preferably, the viscosity of the liquid component according to the present invention is 1 to 1,000 cp. At below 1 cp, the liquid component mixes with the powdery component so incompletely that it can possibly be contaminated with unreacted powders. At higher than 1,000 cp, on the other hand, it reacts with the powdery component so rapidly that the curing time can shorten, thus making tissue conditioning inconvenient.

As mentioned previously, with respect to tissue conditioners, there are no definite standards relating to measuring their gelling-initiation time or their time for manipulation. In the present invention, therefore, the time for manipulation was found by measuring the change-with-time in the torque of the powder/liquid mixtures with increases in their viscosity by means of a cone/plate type of viscometer. In view of clinical manipulation, the gelling-initiation time is thus defined by a time corresponding to the torque value (about 0.5N·cm) obtained when the powder/liquid mixture is applied on the mucosal surface of a denture plate, thereby determining the time for manipulation. Further, this procedure was used to measure the time for manipulation at 20° C. and 25° C. of materials in which powdery components of 150-200 mesh and not higher than 200 mesh were used.

In order to make an investigation of how easily the powder/liquid mixtures were separated from denture plates, they were pressed against an acrylic plate with a thickness of 2 mm and, then, dipped in 37° C. distilled water for 3 days, and measure was made according to the ordinary clinical manipulation.

EXAMPLES

Illustrative examples of the dental composition according to the present invention will now be explained.

EXAMPLE 1

A mixture of 90 mol % of butyl methacrylate with 10 mol % of ethyl methacrylate purified by alkali washing and distillation under reduced pressure was subjected to suspension polymerization in an aqueous solution of gelatin to prepare a copolymer of butyl methacrylate with ethyl methacrylate. For experimentation, 1.1 g of the obtained powders were mixed with 1.0 g of butyl phthalyl butyl glycolate (BPBG) for 30 seconds.

EXAMPLE 2

A mixture of 80 mol % of butyl methacrylate with 20 mol % of ethyl methacrylate was subjected to suspension polymerization in a similar manner as described in Example 1 to prepare a copolymer of butyl methacrylate with ethyl methacrylate. For experimentation, 1.1 g of the obtained powders were mixed with 1.0 g of dibutyl phtalate (DBP) for 30 seconds.

EXAMPLE 3

Butyl methacrylate and ethyl methacrylate were separately subjected to suspension polymerization in a similar manner as described in Example 1 to prepare PBMA and PEMA, respectively, which were then fully mixed together at a ratio of 4.0 g to 1.0 g. For experimentation, 1.1 of the obtained mixture were mixed with 1.0 g of butyl phthalyl butyl glycolate (BPBG) for 30 seconds.

COMPARATIVE EXAMPLE 1

For comparative experimentation, 1.1 g of the powders sold by G-C Dental Industrial Corp. under the trade name of GC Soft Liner were mixed with 1.0 g of liquid for 30 seconds. In this example, the powdery component was a resin based on ethyl methacrylate, whereas the liquid component was a liquid mixture of butyl phthalyl butyl glycolate (BPBG) with ethanol.

COMPARATIVE EXAMPLE 2

The powdery component used was PBMA alone, whereas the liquid component used was butyl phthalyl butyl glycolate (BPBG). For experimentation, both were mixed and kneaded together for 30 seconds.

FIGS. 1 and 2 show the changes-with-time at 20° C. and 25° C. in the torque of the respective materials with increases in their viscosity.

There are no standards relating to the gelling-initiation time of tissue conditioners. Thus, investigations were carried out of time when a tissue conditioner comprising a mixture of the powdery component with the liquid component is to be clinically applied on the mucosal surface of a denture plate. With a cone/plate type of rotary viscometer, the changes-with-time in the torque of that mixture with increases in its viscosity were then measured to find the point of time showing a torque value of 0.5N·cm, which was determined as the gelling-initiation time.

From a comparison of the gelling-initiation times at 20° C. in FIG. 1, it is noted that the comparative examples are shorter than the examples.

This tendency holds substantially for FIG. 2, but the gelling-initiation times in FIG. 2 are closer to each other than those in FIG. 1.

However, the gelling-initiation time of tissue conditioners is a factor that is clinically important in view of manipulatability. Depending upon cases, a longer time allowed for manipulation between mixing and the gelling-initiation time is often favorable.

Of importance to tissue conditioners is that:

(1) they maintain a combined elastic/viscous properties in the oral cavity over an extended period of time; and (2) they possess an adhesion strength sufficient for allowing them to remain bonded to the surfaces of denture plates in the oral cavity over an extended period of time. From FIGS. 1 and 2, it is said that Examples 1-3 are more preferable to Comparative Examples 1-2.

While the dental composition according to the present invention is actually mixed and applied on the mucosal surface of a denture plate to place it in the oral cavity, it is preferred that the mouth be washed out several times in order to cool off the tissue conditioner. The compositions of the powdery and liquid components of Examples 1-3 and Comparative Examples 1-2 and the results of other experiments are summarized in Table 2.

The viscosity of the liquid component of Comparative Example 1 is lower than those of Examples 1-3, because it contains ethanol. However, no particular clinical problem was found in connection with the viscosity of the plasticizer set forth in the examples.

In the examples, butyl phthalyl butyl glycolate (BPBG) and dibutyl phthalate (DBP) were respectively used as the liquid components. However, no problem arises even when benzyl butyl phthalate, benzyl benzoate, ethyl benzoate, butyl benzoate and amyl benzoate are used to this end alone or in combination of two or more.

As already stated, the particle size of the powdery component according to the present invention is desirously 50-600 mesh. Table 2 shows the gelling-initiation times at 20° C. and 25° C. of the tissue conditioners using the powdery components having a particle size of 150-200 mesh and not higher than 200 mesh.

In view of production, the particle size of the powdery component is preferably 150-300 mesh. In order to regulate the gelling-initiation time, however, a powdery component having a particle size of at most 50 mesh or at least 600 mesh may be used. For odor and taste set forth in Table 2, a mixture of the powdery with liquid components was placed in the oral cavity of each of the present four inventors.

Table 2 summarizes the amounts of powder and liquid, the viscosity of liquid at 25° C., the time for manipulation, odor and taste and the results of peeling tests from the dental plate in Examples 1-3 and Comparative Examples 1-2.

Figure 3:
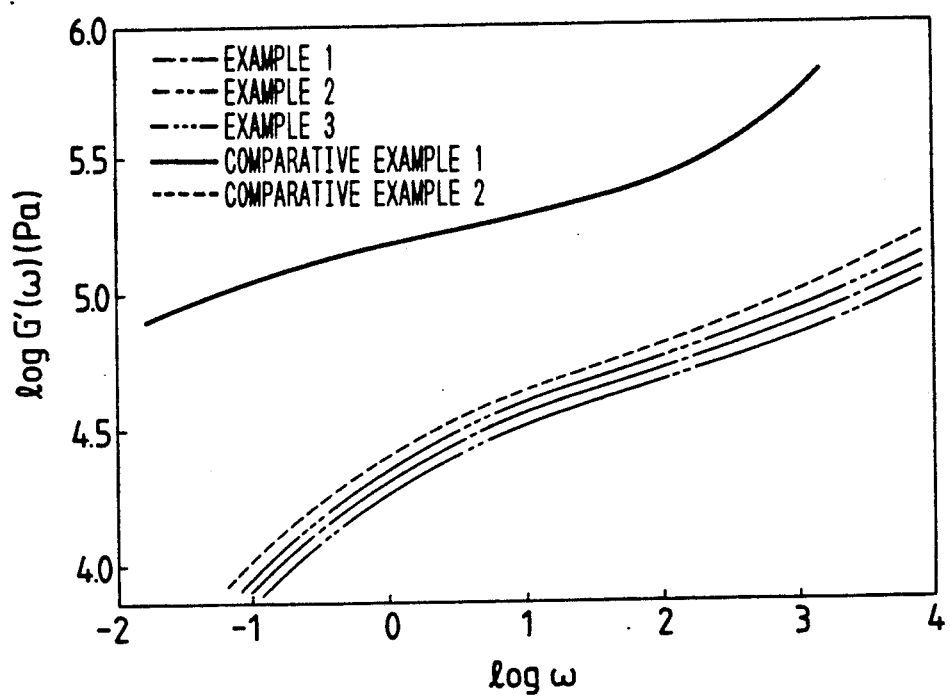
FIG. 3 is a graphical view showing storage modulus G' master curves of examples of the dental composition according to the present invention and comparative examples.

Further, the results of dynamic viscoelasticity of the five materials are set forth in FIG. 3, in which the respective curves refer to the data of Examples 1-3 and Comparative Examples 1-2. Such powders and liquids were cast into a glass mold at the specified ratios and gelated to prepare test pieces. After allowed to store at room temperature for 24 hours, they were subjected to forced shear vibrations to measure their dynamic viscoelasticity. The above curves are master curves of storage modulus G', which are obtained by the application of the time-temperature superposition principle for finding the frequency and temperature dependence of a storage modulus G'. As the storage modulus G' is one of important viscoelastic properties for estimating actual aspects of material can be noted from FIG. 3, the composition according to the present invention has its storage modulus G' smaller than that of the conventional material of Comparative Example 1 over the entire frequency range, and so is a soft and flexible material. As already stated, the properties required for tissue conditioners are that they act as an elastomer with respect to an instantaneously applied force, and they show their own plasticity, when a weak oppresive force is applied to material, as encountered in the recovery of oral mucose's deformation. From such a viewpoint, it is noted that the composition according to the present invention is superior to the conventional materials, as will be clearly understood from FIG. 3.

EFFECT OF THE INVENTION

As detailed above by way of the examples, etc., the mixture of poly butyl methacrylate with poly ethyl methacrylate or the copolymer of butyl methacrylate with ethyl methacrylate is used as the powdery component of a tissue conditioner composition and butyl phthalyl butyl glycolate (BPBG), dibutyl phthalate (DBP), benzyl butyl phthalate, benzyl benzoate, ethyl benzoate, butyl benzoate and/or amyl benzoate are used as the liquid component. As the liquid component of the dental composition according to the present invention is free from ethanol, it gives no stimuli to the mucosal surface of a patient and emit no offensive odor. Thus, it is unlikely to make patients unpleasant.

Furthermore, even when the present composition is applied to a denture plate composed of a material based on MMA for the purpose of tissue conditioning, it is unlikely that the surface of the denture plate may dissolve, or deform or crack due to its swelling by ethanol. It is also unlikely that the denture plate may remain bonded mechanically to the tissue conditioner because of its surface dissolving after curing, when it is separated from the denture plate. Thus, the present composition can easily be separated from the denture plate. As a result of dynamic viscoelastic measurment, it has been found that the dental compositions according to the present invention maintain softness and flexibility over an extended period of time. Thus, the new materials have their properties improved over those of conventional materials. Although the liquid component contains no ethanol, the powdery component can swell and have increased affinity with respect to the liquid component. After mixing, the mixture of the powdery with liquid components can be rapidly cured so that it can possess elasticity in combination with adhesion, both required for tissue conditioners.

At below 200 mesh, materials containing no ethanol and using a polymer of poly butyl methacrylate alone as the powdery component show the shortest gelling-initiation time and are poor in manipulatability irrespective of the conditions applied. However, if the mixture of poly butyl methacrylate with poly ethyl methacrylate is used as the powdery component, then it is possible to extend the gelling-initiation time and improve manipulatability.

In terms of materials, denture plates generally used in dentistry are mainly broken down into metallic and plastic types. Generally formed of gold and Ti alloys, the metallic type is expensive and complicate to prepare. For the plastic type, on the other hand, acrylic and polysulfone base materials are used. However, acrylic materials are now mainly used in view of manipulatability, material cost and easiness with which the steps of production are carried out. Situation being like this, the dental composition according to the present invention in which the liquid component is rid of ethanol is said to be useful in dental treatment for both patients and clinicians.

TABLE 2

Compositions of powdery and liquid components in examples and comparative examples and results of experiment

|  | Example 1 | Example 2 | Example 3 | Comparative Example 1 | Comparative Example 2 |
|---|---|---|---|---|---|
| Powder | Butyl methacrylate (90 mol %)-ethyl methacrylate (10 mol %) copolymer | Butyl methacrylate (80 mol %)-ethyl methacrylate (20 mol %) copolymer | Poly butyl methacrylate (4.0 g) and poly ethyl methacrylate (1.0 g) | "GC Soft Liner" powder (resin based on methacrylate) | Polymer of poly butyl methacrylate alone (PBMA) 100% |
| Amount (g) | 1.1 | 1.1 | 1.1 | 1.1 | 1.1 |
| Liquid | Butyl phthalyl butyl glycolate (BPBG) | Dibutyl phtalate (DBP) | Butyl phthalyl butyl glycolate (BPBG) | "GC Soft Liner" liquid (liquid mixture of butyl phthalyl butyl glycolate with ethanol | Butyl phthalyl butyl glycolate (BPBG) |
| Amount (g) | 1.0 | 1.0 | 1.0 | 1.0 | 1.0 |
| Viscosity of liquid (cp. 25° C.) | 54 | 16 | 54 | 12 | 54 |
| Gelling-initiation | | | | | |

TABLE 2-continued

Compositions of powdery and liquid components in examples and comparative examples and results of experiment

|  | Example 1 | Example 2 | Example 3 | Comparative Example 1 | Comparative Example 2 |
|---|---|---|---|---|---|
| time (min:sec) 150~200 meshes | | | | | |
| 20° C. | 7:30 | 8:00 | 6:30 | | 4:30 |
| 25° C. | 6:30 | 7:00 | 5:30 | | 4:00 |
| Not higher than 200 meshes | | | | | |
| 20° C. | 3:30 | 4:00 | 3:40 | 4:40 | 2:00 |
| 25° C. | 3:00 | 3:30 | 3:10 | 2:40 | 1:50 |
| Smell and taste | Tasteless and smell-less | Tasteless and smell-less | Tasteless and smell-less | Smelling of ethanol | Tasteless and smell-less |
| Separation from denture plate | Easy | Easy | Easy | Difficult | Easy |

What is claimed is:

1. A denture plate adhesive soft liner or gelling tissue conditioner adapted to adhere to a denture plate which may dissolve, deform, crack, swell or drop strength by the action of ethanol, which consists essentially of a powdery component and a liquid component free of ethanol which are mixed together, wherein said powdery component is at least one copolymer selected from the group consisting of a copolymer of 100 mol % of butyl methacrylate with 5 to 50 mol % of ethyl methacrylate, or a mixture of 100 mol % polybutyl methacrylate with 5 to 50 mol % polyethyl methacrylate; and said liquid component free of ethanol is at least one selected from the group consisting of butyl phthalyl butyl glycolate, dibutyl phthalate, benzyl butyl phthalate, benzyl benzoate, ethyl benzoate, butyl benzoate and amyl benzoate.

2. The denture plate adhesive soft liner or gelling tissue conditioner as claimed in claim 1, wherein said powdery component has a molecular weight of 100,000 to 1,500,000.

3. The denture plate adhesive soft liner or gelling tissue conditioner as claimed in claim 1, wherein said powdery component has a particle size of 50 mesh to 600 mesh.

4. The denture plate adhesive soft liner or gelling tissue conditioner as claimed in claim 1, wherein said liquid component has a viscosity of 1-1000 cp.

5. The denture plate adhesive soft liner or gelling tissue conditioner as claimed in claim 1, wherein said powdery component has a particle size of 150 mesh to 300 mesh.

* * * * *